(12) United States Patent
Newcomb et al.

(10) Patent No.: US 7,819,905 B2
(45) Date of Patent: Oct. 26, 2010

(54) SELF DRILLING BONE SCREW

(75) Inventors: Gene Newcomb, Plymouth, MN (US); Craig Hahne, Maple Grove, MN (US); Jason Piehl, Apple Valley, MN (US); Kevin V. Guenther, Carver, MN (US)

(73) Assignee: Zimmer Spine, Inc., Minneapolis, MN (US)

( * ) Notice: Subject to any disclaimer, the term of this patent is extended or adjusted under 35 U.S.C. 154(b) by 1132 days.

(21) Appl. No.: 11/015,895

(22) Filed: Dec. 17, 2004

(65) Prior Publication Data

US 2006/0149263 A1 Jul. 6, 2006

(51) Int. Cl.
*A61B 17/04* (2006.01)
*A61B 17/86* (2006.01)
*A61F 2/08* (2006.01)

(52) U.S. Cl. .................. 606/311; 606/312; 606/318

(58) Field of Classification Search .......... 606/300, 606/311, 312, 318; 411/386, 387.1, 394, 411/919; 408/223–225
See application file for complete search history.

(56) References Cited

U.S. PATENT DOCUMENTS

| | | | | |
|---|---|---|---|---|
| 3,564,947 A | * | 2/1971 | Maier | .................. 408/211 |
| 3,779,664 A | * | 12/1973 | Caley et al. | .................. 408/225 |
| 4,605,347 A | * | 8/1986 | Jodock et al. | ............... 408/224 |
| 5,334,204 A | | 8/1994 | Clewett et al. | |
| 5,544,993 A | | 8/1996 | Harle | |
| 5,797,914 A | * | 8/1998 | Leibinger | .................. 606/308 |
| 5,871,486 A | | 2/1999 | Huebner et al. | |
| 5,925,048 A | | 7/1999 | Ahmad et al. | |
| 5,951,560 A | | 9/1999 | Simon et al. | |
| 5,964,766 A | | 10/1999 | Shaw | |
| 6,508,820 B2 | | 1/2003 | Bales | |

* cited by examiner

*Primary Examiner*—Thomas C Barrett
*Assistant Examiner*—Andrew Yang
(74) *Attorney, Agent, or Firm*—Crompton, Seager & Tufte, LLC.

(57) ABSTRACT

A self-drilling bone screw includes a screw body centered on a longitudinal axis and having an external thread winding. The bone screw has a head portion at one end of the screw body and a drill point at the other end. The drill point has two blades, each having a cutting lip and a primary relief surface trailing from the cutting lip. The two blades defining a flute between them. The flute has an opening to the side of the screw body, which opening spans an obtuse angle, such as about 120°, about the longitudinal axis. The primary relief surfaces have a lip relief angle of about 30°. The drill point has a point angle of about 100°.

16 Claims, 4 Drawing Sheets

SELF DRILLING BONE SCREW

FIELD OF THE INVENTION

The invention relates generally to bone screws used in orthopedic surgeries. More particularly, the invention relates to a self-drilling bone screw.

BACKGROUND OF THE INVENTION

Bone screws are widely used in orthopedic surgical procedures such as spinal surgeries. Typically, bone screws are used to secure structures, such as spinal plates and spinal rod connectors, to various bone portions to stabilize the bone portions relative to others. For example, cervical plates are typically secured to vertebrae with bone screws for stabilization of the cervical spine. Likewise, occipital plates are typically secured to the back of the skull with bone screws for attaching spinal rods.

To attach a bone screw to the bone, the dense outer layers of the bone, or cortical bone, are typically penetrated. The softer inner portions of the bone, or cancellous bone, are typically at least partially penetrated. Various procedures are used to install bone screws. Some include drilling a pilot hole in the bone and tapping the pilot hole to form an internal screw thread before a bone screw is driven into the pre-drilled and pre-tapped pilot hole. Others include driving self-tapping screws into pre-drilled pilot holes. Still others include driving self-drilling screws directly into the bone without pre-drilling or pre-tapping.

In surgical operations, it is generally desirable to minimize the length of time when the surgical wounds remain open and to ensure the quality of the operations. Consistent with this goal, there is therefore a need for bone screws that can be accurately, quickly and securely fastened to bones.

SUMMARY OF THE INVENTION

In one embodiment of the invention, a bone screw has a screw body centered on a longitudinal axis and having proximal and distal ends; a head portion at the proximal end; and a drill point at the distal end. At least a portion of the screw body has an external thread winding about the longitudinal axis. The drill point has two blades. Each blade has a cutting lip and a primary relief surface trailing from the cutting lip and having a trailing edge opposite the cutting lip across the relief surface. The two blades define a flute between them with the first blade leading the second blade. When viewed from the distal end along the longitudinal axis, the cutting lip of each blade is at an obtuse angle from trailing edge of the primary relief surface of the opposite blade across the flute between the two blades. The primary relief surface can have a lip relief angle of about 30°. The point angle of the drill point can be about 100°.

In another embodiment of the invention, a bone screw includes a screw body centered on a longitudinal axis and having two ends; a head portion at one end of the screw body; and a drill point at the other end of the screw body. At least a portion of the screw body has an external thread winding about the longitudinal axis. The drill point having two and only two blades, each having a cutting lip and a primary relief surface trailing from the cutting lip. The two blades defining a flute between them. The flute having an opening on a side wall of the screw body. The opening spans an obtuse angle, such as about 120°, about the longitudinal axis.

BRIEF DESCRIPTION OF THE DRAWINGS

Other objects and advantages of the invention will become apparent upon reading the following detailed description and upon reference to the drawings in which.

Figure 1:
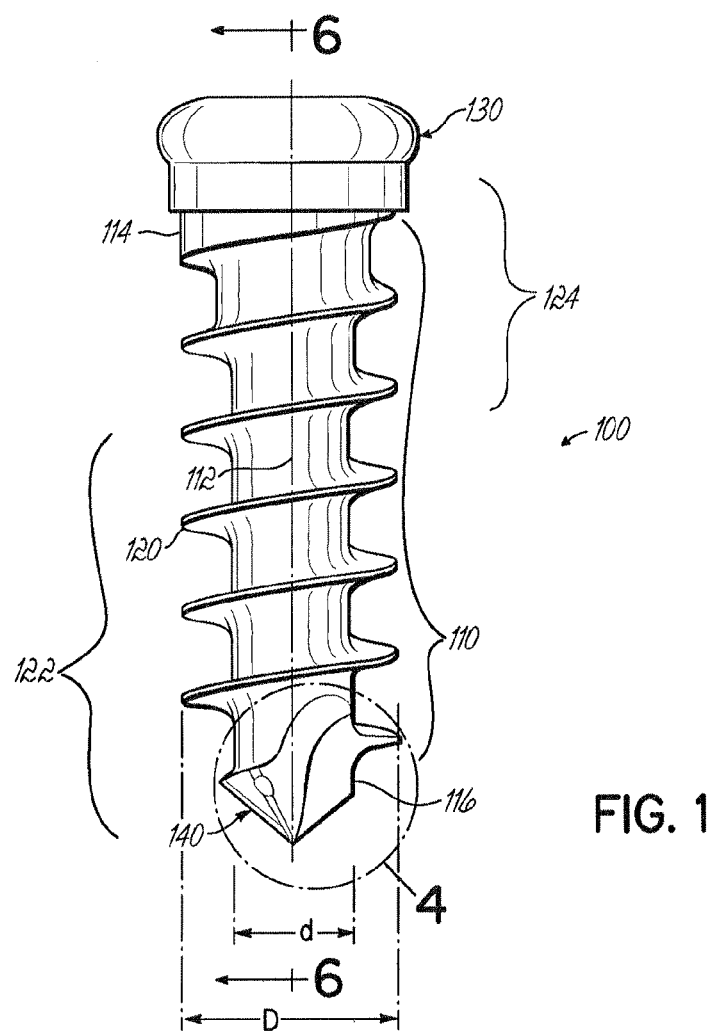
FIG. 1 is a main view of a self-drilling screw according to an embodiment of the invention.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF SPECIFIC EMBODIMENTS

Referring to FIG. 1, in an illustrative embodiment of the invention, a bone screw 100 includes a screw body 110 centered on a longitudinal axis 112. The screw body 110 is elongated had has a proximal end 114 and distal end 116. The screw body 110 also has a helical external thread 120 winding about the longitudinal axis 112. The bone screw 100 further has a head portion 130 connected to the screw body 110 at the proximal end 114 and a drill point 140 connected to the screw body 110 at the distal end 116.

Figure 2:
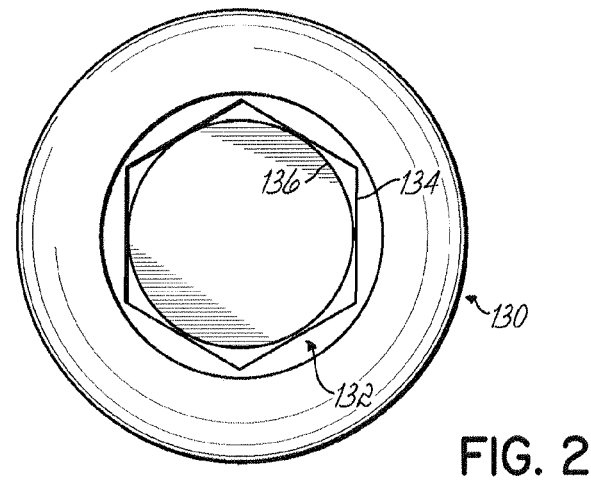
FIG. 2 is a top view, showing the head portion, of the self-drilling screw shown in FIG. 1.
Figure 6:
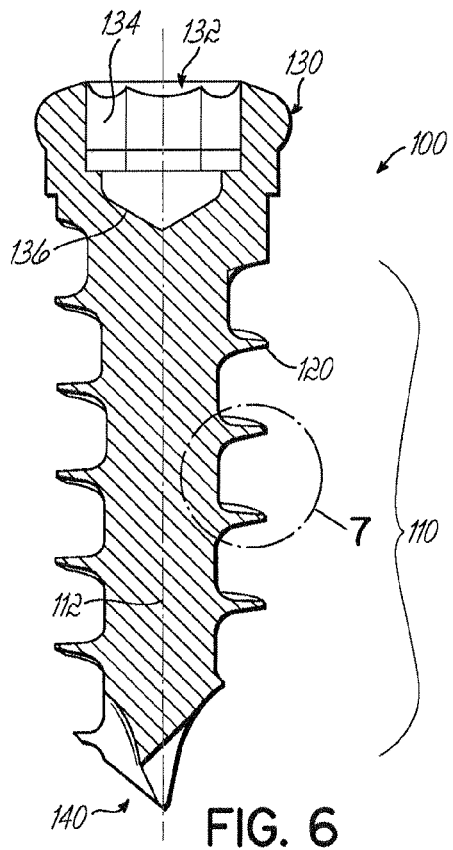
FIG. 6 is a cross-sectional view through the longitudinal axis of the self-drilling screw shown in FIG. 1.

With additional reference to FIGS. 2 and 6, the head portion 130 can take the form of any suitable screw head configuration. In the embodiment shown in FIGS. 2 and 6, the head portion 130 is a generally round screw head with a socket 132 for receiving the tip of a driver (not shown). The socket 132 has a hexagonal hollow portion 134 and a bottom recess 136.

Figure 3:
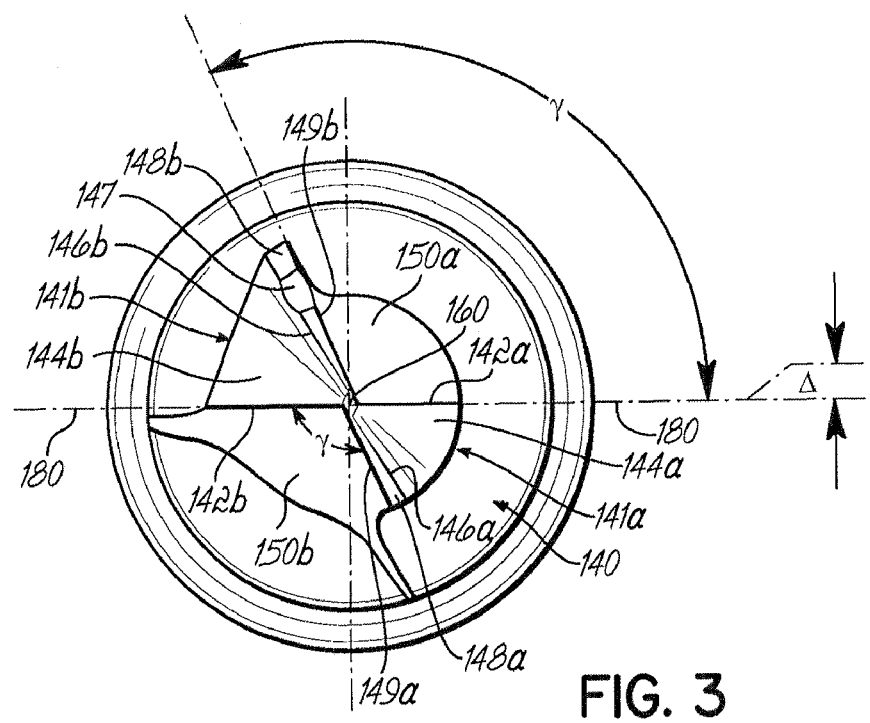
FIG. 3 is a bottom view, showing the drill point, of the self-drilling screw shown in FIG. 1.
Figure 4:
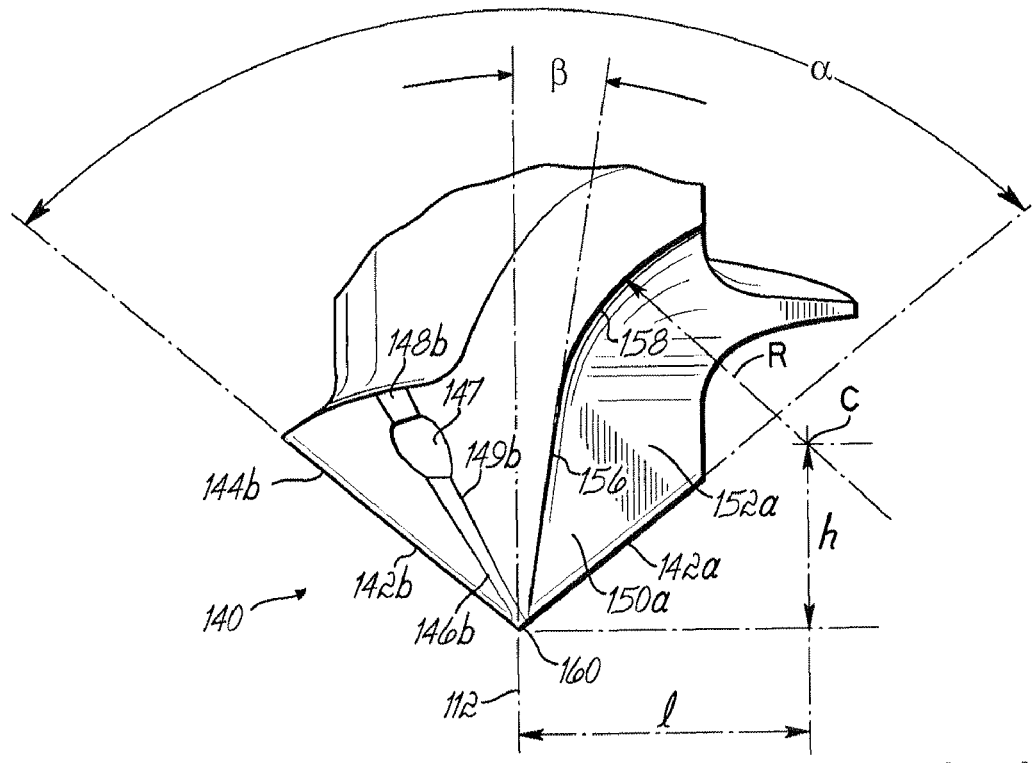
FIG. 4 is an enlarged portion of the main view of FIG. 1, showing the details of the drill point.
Figure 5:
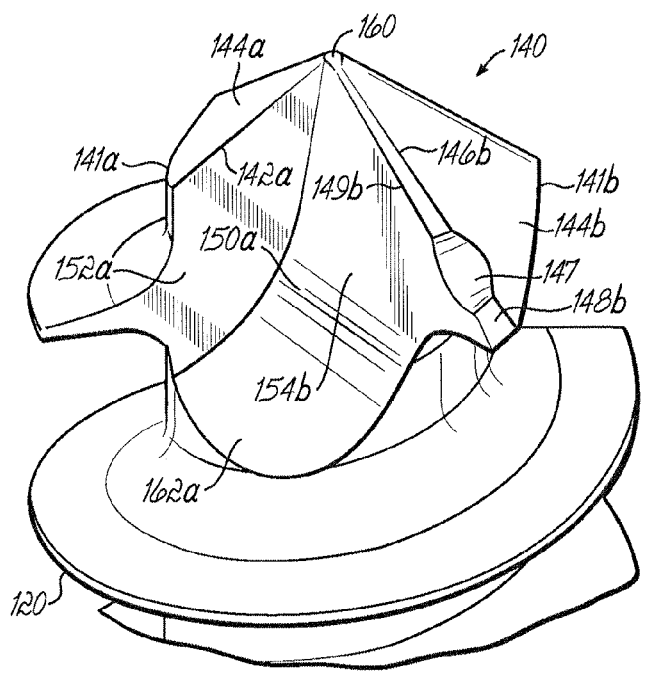
FIG. 5 is a perspective view of the drill point of the self-drilling screw shown in FIG. 1.

Referring further to FIGS. 3, 4 and 5, the drill point 140 is adapted to penetrate bone and has two blades 141*a* and 141*b*. The drill point will be described further using the following definitions:

Chisel Edge: The edge at the end of the web that connects the cutting lips;

Flutes: Grooves formed in the body of the drill point to provide cutting lips and to permit removal of cutting debris;

Cutting Lips: The cutting edges extending generally from the tip of the drill point to the periphery;

Lip Relief: The axial relief on the drill point;

Lip Relief Angle: The axial relief angle at the outer corner of the cutting lip; it is measured by projection into a plane tangent to the periphery at the outer corner of the cutting lip;

Point Angle: The vertex angle of the virtual cone generated by the lines collinear with their respective cutting lips when the drill point is rotated about the longitudinal axis. When a drill point has only two blades, the point angle is the same as the angle between the cutting lips projected upon a plane parallel to the drill axis and parallel to the two cutting lips;

Relief: The result of the removal of tool material behind or adjacent to the cutting lip and leading edge of the land to provide clearance and prevent rubbing between the trailing portions of the blade and the bone; and Web: The central portion of the body that joins the blades; the extreme end of the web can form a chisel edge on a two-flute drill.

The blade 141a has a cutting lip 142a, a primary relief surface 144a trailing from the cutting lip 142a and having a trailing edge 146a, and a secondary relief surface 148a trailing from the trailing edge 146a and having a trailing edge 149a. Likewise the blade 141b has a cutting lip 142b, a primary relief surface 144b trailing from the cutting lip 142b and having a trailing edge 146b, and a secondary relief surface 148b trailing from the trailing edge 146b and having a trailing edge 149b. The blades 141a and 141b are approximately 180° apart about the longitudinal axis 112. The blades 141a and 141b can have different dimensions and appearances due to the intersection between the blades 141a and 141b and the helical external thread 120 and other features near the tip of the screw body 110 but are otherwise symmetrical with each other according to a two-fold symmetry about the longitudinal axis 112. For example, a recess 147 appears on the secondary relief surface 148b of the blade 141b as a result of the secondary relief surface intersecting two adjacent windings of the external thread 120 near the bottom of the trough between the windings.

The blades 141a and 141b form two flutes 150a and 150b between and on either side of the blades 141a and 141b. As best shown in FIG. 3, flute 150a or 150b spans an obtuse angle γ, about the longitudinal axis 112, to the side of the bone screw 100. In this illustrative embodiment, the angle γ is about 120°. Other obtuse angles, such as from about 110° to about 130°, can also be used. In this illustrative embodiment of the invention, the cutting lips 142a and 142b and trailing edges 149a and 149b are all straight. The angle γ spanned by the flutes 150a and 150b are thus measured, respectively, by the angle between the cutting lip 142a and trailing edge 149b and the angle between cutting lip 142b and trailing edge 149a.

The drill point 140 has a point angle a of about 100° in this illustrative embodiment of the invention. Other angles can be used, such as from about 90° to about 110°.

The cutting lips 142a and 142b lie in respective virtual planes that are parallel to, but offset from, the longitudinal axis 112 and offset from each other. In the embodiment shown in FIG. 3, each cutting lip 142a or 142b is offset from a plane 180 passing through the longitudinal axis 112 by a distance $\Delta$ of about 13 to 380 μm. The blades 141a and 141b overlap each other when viewed in the direction parallel to the planes passing through the cutting lips 142a and 142b. That is, a plane 180 passing through the longitudinal axis 112 and parallel to the cutting lips 142a and 142b intersects both blades 141a and 141b.

A web 160 connects the two blades 141a and 141b. The web 160 is formed by the drill tip material remaining after the flutes 150a and 150b are cut and has a finite width, providing mechanical strength to the tip of the drill point. The tip of the web 160 in this illustrative embodiment is cone-shaped but can be any other shape suited for a particular application. For example, a chisel edge can be formed at the tip.

The primary lip relief surfaces 144a and 144b have a lip-relief angle of about 30° in the illustrative embodiment of the invention, but can be other suitable angles as well, such as from about 25° to about 35°. The secondary lip relief surfaces 148a and 148b are inclined further relative to the plane perpendicular to the longitudinal axis 112 than the primary lip relief surfaces by about 20° or other suitable angle.

Referring more particularly to FIGS. 4 and 5, the flute 150a, is formed with (a) a planar surface 152a, which is parallel to the longitudinal axis 112 and is bound on the drill point side by the cutting lip 142a of the blade 141a; (b) a planar surface 154b behind the blade 141b; and (c) a curved surface 162a joining the two planar surfaces 152a and 154b. The planar surface 152a intersects the planar surface 154b at a straight line segment 156, which is at an angle β (about 8° in this example) from the longitudinal axis 112. The curved surface 162a intersects the planar surface 152a at an arcuate line segment 158. In this example, the arcuate line segment 158 is a circular segment with a radius R (about 1.6 mm), with the center C of the circle positioned at a height h (about 1.2 mm) along the longitudinal axis 112 and lateral distance l (about 1.8 mm) from the apex of the drill point. Other suitable dimensions can be used to achieve desired performance in specific applications.

Referring again to FIGS. 1 and 6, the screw body 110 with the thread 120 has a substantially constant major diameter D, which is the maximum diameter of the screw body 110. A distal portion 122 of screw body 110 also has a substantially constant minor diameter d, which is the minimum diameter of the screw body 110. A proximal portion 124 of the screw body 110, in contrast, has a tapered profile, with a gradually increasing minor diameter towards the head portion 130. The increased minor diameter near the head portion 130 enhances the engagement between the bone screw 100 and the cortical bone layers of the bone into which the bone screw 100 is driven. In several embodiments of the invention, the length of the screw body 110 range from about 10 mm to 18 mm. The major diameter D of the screw body 110 is about 4.2 to 4.6 mm. The minor diameter d for the distal portion 122 is about 2.3 mm. The minor diameter d for the proximal portion 124 gradually increases towards the head portion 130 over a length of about 5.2 mm with an approximately 9° divergence with respect to the longitudinal axis 112. Other dimensions can also be used depending on the specific application.

Figure 7:
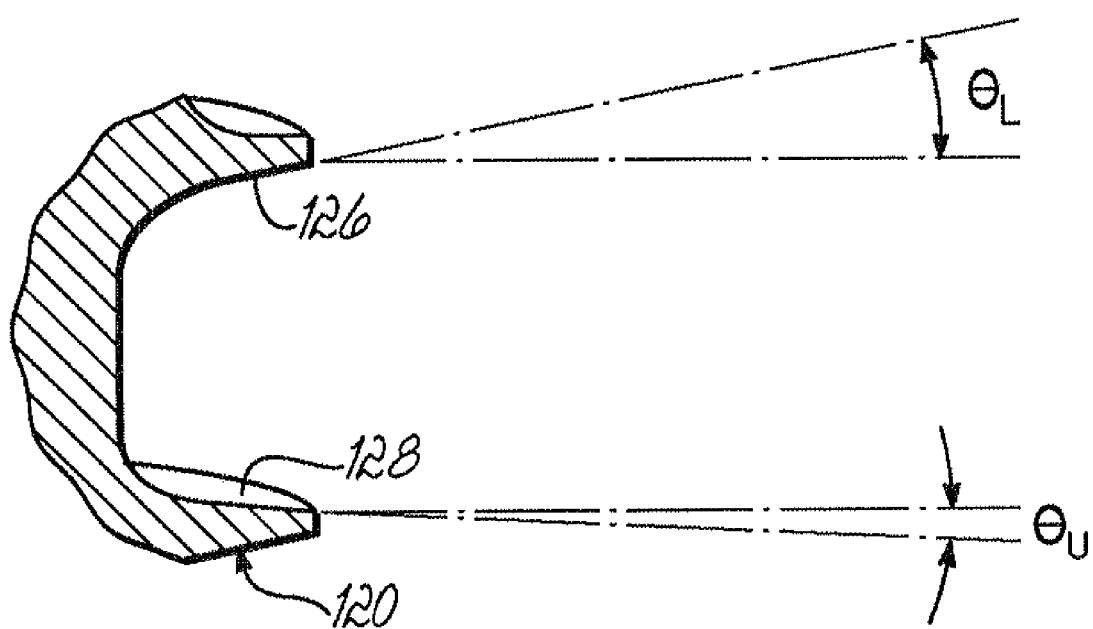
FIG. 7 is an enlarged view of a portion of the cross-sectional view in FIG. 6 showing in greater detail a portion of the external thread.

The external thread 120, as illustrated in detail in FIG. 7, has an lower surface 126, facing the head portion 130, and upper surface 128, facing the drill point. The lower surface 126 slopes up radially at an angle $\theta_L$ with respect to a plane perpendicular to the longitudinal axis 112. The upper surface 128 slopes down radially at an angle $\theta_U$ with respect to a plane perpendicular to the longitudinal axis 112. $\theta_L$ is about 10°, and $\theta_U$ is about 3° in this illustrative embodiment of the invention, but other angles can also be used.

The bone screws can be made of any material for implantation, including biocompatible materials such as titanium and stainless steel.

The bone screws according to the embodiments disclosed above provide more aggressive cutting than conventional bone screws and thus is more easily driven into bones without the need for pre-drilling of pilot holes or pre-tapping. The features of the bone screws according to the invention also facilitate secure engagement of the bone screws to bone.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed is:

1. A bone screw, comprising:
   a screw body having proximal and distal ends and a central longitudinal axis, at least a portion of the screw body having an external thread winding about the central longitudinal axis;
   a head portion connected to the body at the proximal end;
   a drill point connected to the body at the distal end, the drill point having a first blade and a second blade with the first blade leading the second blade;
   the first blade having a cutting lip, a primary relief surface trailing from the cutting lip of the first blade having a trailing edge, and a secondary relief surface trailing from the trailing edge of the primary relief surface of the first blade, the secondary relief surface of the first blade having a trailing edge, wherein the trailing edge of the secondary relief surface of the first blade is a straight edge not passing through the central longitudinal axis;
   the second blade having a cutting lip, a primary relief surface trailing from the cutting lip of the second blade having a trailing edge, and a secondary relief surface trailing from the trailing edge of the primary relief surface of the second blade, the secondary relief surface of the second blade having a trailing edge, wherein the trailing edge of the secondary relief surface of the second blade is a straight edge not passing through the central longitudinal axis;
   a first flute defined between the trailing edge of the secondary relief surface of the first blade and the cutting lip of the second blade; and
   a second flute defined between the trailing edge of the secondary relief surface of the second blade and the cutting lip of the first blade;
   wherein the cutting lip of the second blade and the trailing edge of the secondary relief surface of the first blade define an obtuse angle.

2. The bone screw of claim 1, wherein the drill point is adapted to penetrate bone.

3. The bone screw of claim 2, wherein the drill point has a point angle of between about 90° and about 110°.

4. The bone screw of claim 3, wherein the drill point has a point angle of about 100°.

5. The bone screw of claim 2, wherein the cutting lip of each of the first and second blades lies in a respective plane parallel to, and offset from, the central longitudinal axis of the screw body.

6. The bone screw of claim 5, wherein a plane passing through the central longitudinal axis and parallel to the cutting lips intersects the first and second blades.

7. The bone screw of claim 6, the drill point further comprising a web portion having a finite width and connecting the two cutting lips.

8. The bone screw of claim 1, wherein the primary lip relief surface of each blade has a lip relief angle of from about 25° to about 35°.

9. The bone screw of claim 8, wherein the primary lip relief surface of each blade has a lip relief angle of about 30°.

10. The bone screw of claim 8, wherein the secondary relief surface of each blade has a relief angle of about 20° from the primary relief surface of the respective blade.

11. The bone screw of claim 1, wherein the obtuse angle is about 120°.

12. The bone screw of claim 11, wherein the primary lip relief surface of each blade has a lip relief angle of about 30°.

13. The bone screw of claim 1, wherein at least a portion of the screw body having the external thread has a constant major diameter along the central longitudinal axis and has a proximal portion having an increasing minor diameter towards the head portion.

14. The bone screw of claim 1, wherein:
   the first flute is defined by a first planar surface, a second planar surface intersecting the first planar surface, and a first curved surface intersecting both the first planar surface and the second planar surface; and
   the second flute is defined by a third planar surface, a fourth planar surface intersecting the third planar surface, and a second curved surface intersecting both the third planar surface and the fourth planar surface.

15. The bone screw of claim 1, wherein the cutting lip of the first blade is a straight edge and the cutting lip of the second blade is a straight edge.

16. A bone screw, comprising:
   a screw body having proximal and distal ends, at least a portion of the screw body having an external thread;
   a head portion connected to the body at the proximal end;
   a drill point connected to the body at the distal end, the drill point having a first blade and a second blade with the first blade leading the second blade;
   the first blade having a cutting lip, a primary relief surface trailing from the cutting lip of the first blade having a trailing edge, and a secondary relief surface trailing from the trailing edge of the primary relief surface of the first blade, the secondary relief surface of the first blade having a trailing edge, wherein the trailing edge of the secondary relief surface of the first blade is a straight edge;
   the second blade having a cutting lip, a primary relief surface trailing from the cutting lip of the second blade having a trailing edge, and a secondary relief surface trailing from the trailing edge of the primary relief surface of the second blade, the secondary relief surface of the second blade having a trailing edge, wherein the trailing edge of the secondary relief surface of the second blade is a straight edge;
   a first flute defined between the trailing edge of the secondary relief surface of the first blade and the cutting lip of the second blade;
   a second flute defined between the trailing edge of the secondary relief surface of the second blade and the cutting lip of the first blade;
   wherein the cutting lip of the second blade and the trailing edge of the secondary relief surface of the first blade define an obtuse angle; and
   a recess in the secondary relief surface of the second blade, the recess separating a first portion of the secondary relief surface of the second blade from second portion of the secondary relief surface of the second blade.

* * * * *